United States Patent
Bell et al.

(10) Patent No.: US 8,317,790 B2
(45) Date of Patent: Nov. 27, 2012

(54) SURGICAL STAPLE LINE REINFORCEMENTS

(75) Inventors: Deborah W. Bell, Flagstaff, AZ (US);
Samuel M. Date, Flagstaff, AZ (US);
Jared G. Ragone, Newark, DE (US);
Michael S. Winterling, Landenberg, PA (US)

(73) Assignee: W. L. Gore & Associates, Inc., Newark, DE (US)

( * ) Notice: Subject to any disclaimer, the term of this patent is extended or adjusted under 35 U.S.C. 154(b) by 1030 days.

(21) Appl. No.: 12/208,394

(22) Filed: Sep. 11, 2008

(65) Prior Publication Data
US 2009/0076510 A1    Mar. 19, 2009

Related U.S. Application Data

(60) Provisional application No. 60/972,516, filed on Sep. 14, 2007.

(51) Int. Cl.
*A61B 17/64* (2006.01)
(52) U.S. Cl. .......................................... 606/75
(58) Field of Classification Search .................. 606/75, 606/151
See application file for complete search history.

(56) References Cited

U.S. PATENT DOCUMENTS

| | | | |
|---|---|---|---|
| 3,054,406 A | 10/1958 | Usher | |
| 2,954,139 A * | 9/1960 | Owens | 215/246 |
| 3,124,136 A | 3/1964 | Usher | |
| 3,953,566 A | 4/1976 | Gore | |
| 3,962,153 A | 6/1976 | Gore | |
| 4,096,227 A | 6/1978 | Gore | |
| 4,187,390 A | 2/1980 | Gore | |
| 4,347,847 A | 9/1982 | Usher | |
| 4,354,628 A | 10/1982 | Green | |
| 4,452,245 A | 6/1984 | Usher | |
| 4,655,221 A | 4/1987 | Devereux | |
| 5,002,551 A | 3/1991 | Linsky et al. | |
| 5,014,899 A | 5/1991 | Presty et al. | |
| 5,040,715 A | 8/1991 | Green et al. | |
| 5,203,864 A | 4/1993 | Phillips | |
| 5,503,638 A * | 4/1996 | Cooper et al. | 623/11.11 |
| 5,575,803 A * | 11/1996 | Cooper et al. | 606/151 |
| 5,702,409 A | 12/1997 | Rayburn et al. | |
| 5,766,188 A * | 6/1998 | Igaki | 606/151 |
| 5,810,855 A | 9/1998 | Rayburn et al. | |
| 5,908,427 A | 6/1999 | McKean et al. | |
| 6,838,884 B1 | 1/2005 | Dagate | |
| 8,062,534 B2 * | 11/2011 | Higgins et al. | 210/787 |

* cited by examiner

*Primary Examiner* — Nicholas Woodall
(74) *Attorney, Agent, or Firm* — Andrea W. Burke

(57) ABSTRACT

A surgical staple line reinforcement is provided for use with a variety of surgical staplers to protect against tissue damage from surgical staples. The surgical staple line reinforcement is made up of a tubular structure of bio-implantable material with one or more stiffening members attached to or integrated within the tubular structure to resist, prevent or inhibit movement, rotation, or longitudinal compression of the tubular structure.

4 Claims, 2 Drawing Sheets

SURGICAL STAPLE LINE REINFORCEMENTS

CROSS REFERENCE TO RELATED APPLICATION

This application claims priority to provisional application U.S. Ser. No. 60/972,516, filed Sep. 14, 2007.

FIELD OF THE INVENTION

The present invention relates to a surgical staple line reinforcement strengthened to resist movement, rotation, and/or longitudinal compression or bunching during manipulation, positioning and/or deployment of the staple line reinforcement.

BACKGROUND OF THE INVENTION

In some surgical operations, surgical supports, for example, meshes, are employed by surgeons to bridge, repair and/or reinforce tissue defects within a patient, especially those occurring in the abdominal wall, chest wall, diaphragm and other musculo-aponeurotic areas of the body. Surgical supports are disclosed in, for example, U.S. Pat. Nos. 3,054, 406, 3,124,136, 4,347,847, 4,655,221, 6,838,884, and 5,002, 551. During such operations, surgeons employ conventional or known suturing or anchoring techniques to apply such supports to body tissue. For example, U.S. Pat. Nos. 4,652, 245 and 5,203,864 describe methods for suturing or anchoring mesh supports to body tissue, especially during hernia repair operations.

Surgical stapling devices are employed by surgeons to sequentially or simultaneously apply one or more rows of surgical fasteners such as staples or two-part fasteners to body tissue for the purpose of joining segments of body tissue together. Such stapling devices generally consist of a pair of jaws or finger-like structures between which body tissue to be joined is placed. When the instrument is actuated, or "fired," longitudinally moving firing bars contact staple drive members in one of the jaws, thereby pushing surgical staples through the body tissue and into an anvil in the opposite jaw which crimps the staples closed. If tissue is to be removed, a knife blade can be provided to cut between lines of staples. Examples of such instruments are described in U.S. Pat. Nos. 4,354,628, 5,014,899, and 5,040,715, teachings of each of which are incorporated herein by reference.

Surgical stapling devices have found widespread application in surgical operations where body tissue must be joined or removed. When operating on thin tissue, such as thin emphysematous lung tissue, it is important to effectively seal the tissue which can be particularly prone to air leakage. Preventing or reducing air leakage can significantly decrease post operative recovery time. Inhibiting or preventing tearing at the stapled incision site in musculo-aponeurotic areas also significantly decreases recovery time.

Thus, structures for use with surgical stapling devices which enhance sealing at the surgical site and/or reduce tissue tearing are desired.

U.S. Pat. Nos. 5,702,409, 5,810,855, and 5,908,427 describe surgical staple line reinforcement devices and surgical stapling apparatus with tissue bolstering materials.

SUMMARY OF THE INVENTION

The present invention is an improved device for reinforcing surgical staples. The present device is a staple line reinforcement useful in a wide variety of surgical procedures involving surgical staples including, but in no way limited to, lung tissue in lung resection procedures and musculo-aponeurotic areas of the body. The staple line reinforcement of the present invention is considered an important implement in not only establishing improved seals at the surgical site, with reduced possibility of tearing or leaks at the surgical sites through or around surgical staples, but also resisting movement, rotation, and/or longitudinal compression or bunching during manipulation, positioning and/or deployment of the staple line reinforcement.

The staple line reinforcement of the present invention comprises an essentially tubular structure made entirely from an implantable material and one or more stiffening members attached to or integrated with the tubular structure which prevents, inhibits or resists movement, rotation, and/or longitudinal compression or bunching of the staple line reinforcement.

BRIEF DESCRIPTION OF THE DRAWINGS

The operation of the present invention should become apparent from the following description when considered in conjunction with the accompanying drawings, in which.

DETAILED DESCRIPTION OF THE INVENTION

Figure 1:
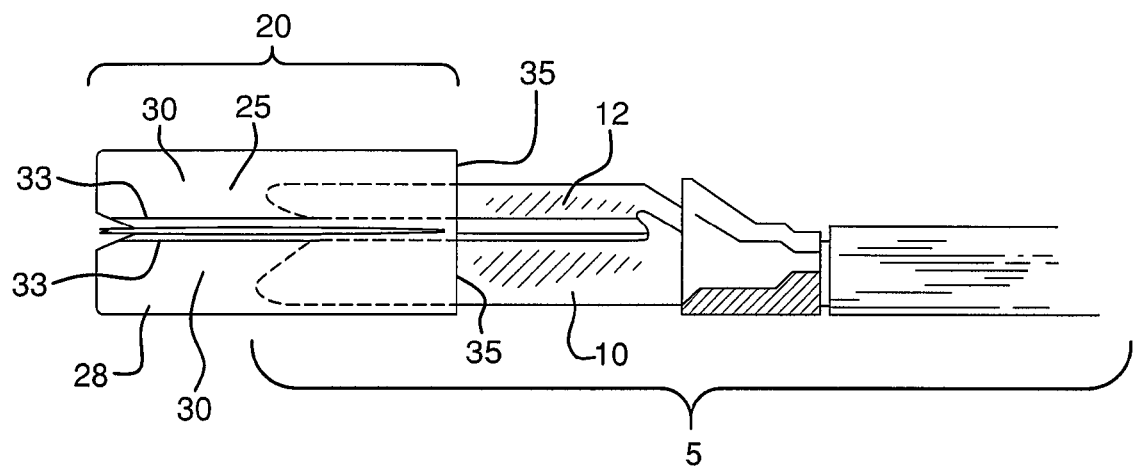
FIG. 1 is a perspective view of a surgical stapler having two surgical staple line reinforcements of the present invention mounted on its stapler arms.

The present invention is an improved device for use in reinforcing staple lines created by a medical stapler. Shown in FIG. 1 are the stapler arms 10, 12 of conventional surgical stapler 5. While commercially available staplers such as depicted in FIG. 1 function well for most cutting and sealing applications, problems have been experienced with the placement of staples in relatively weak and fragile tissue, such as the lung tissue of emphysema patients.

Figure 5:
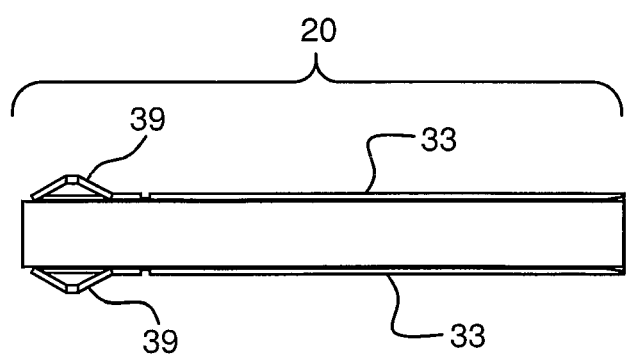
FIG. 5 is bottom view of the surgical staple line reinforcement depicted in FIG. 4.

In the present invention, a staple reinforcement device is provided that overcomes many of the problems previously experienced with such devices. Various embodiments of the staple line reinforcement 20 of the present invention are depicted in FIGS. 1 and 5.

As shown in FIG. 1, the staple line reinforcement 20 comprises a tubular structure 25 adapted to surround the stapler arm 10, 12 and hold the staple line reinforcement in place with at least one face 30 proportioned or sized to receive the rows or lines of surgical staples. The staple line reinforcement further comprises one or more stiffening members 33 attached to or integrated within the tubular structure which prevents, inhibits, or resists movement, rotation, and/or longitudinal compression or bunching of the staple line reinforcement. An opening 35 is provided on at least one end of the tubular structure 25 to allow installation of the staple line reinforcement over the stapler arms.

The staple line reinforcement of the present invention is formed entirely from an implantable material. This allows the staple line reinforcement to be mounted and used with substantially less care than previous staple reinforcement devices. For instance, a slight misalignment of the staple line reinforcement will never result in the accidental attachment of non-implantable material within the patient or an inadequate amount of reinforcement material protecting the tissue.

Further, the tubular reinforcement device of the present invention comprises one or more stiffening members attached to or integrated within the tubular structure which prevents, inhibits or resists movement, rotation, and/or longitudinal compression or bunching of the staple line reinforcement.

Figure 2:
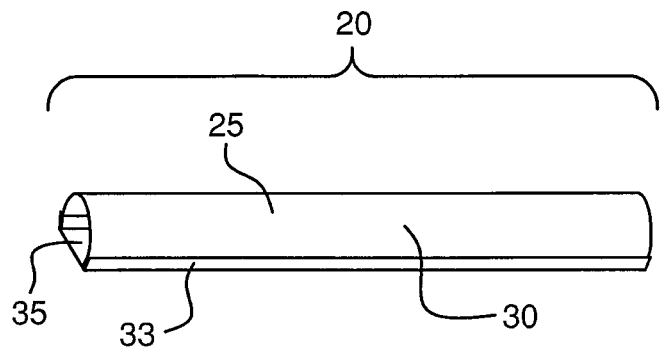
FIG. 2 is a three-quarter isometric view of one embodiment of a surgical staple line reinforcement of the present invention.

In simplest form, as depicted in FIG. 2, the staple line reinforcement 20 comprises a tubular structure 25 having at least one operative face 30 proportioned to reinforce surgical staples at a surgical site. The staple line reinforcement further comprises one or more stiffening members 33 attached to or integrated with the tubular structure and extending the length of the tubular structure to resist, prevent or inhibit movement, rotation, or longitudinal compression of the tubular structure.

Figure 3:
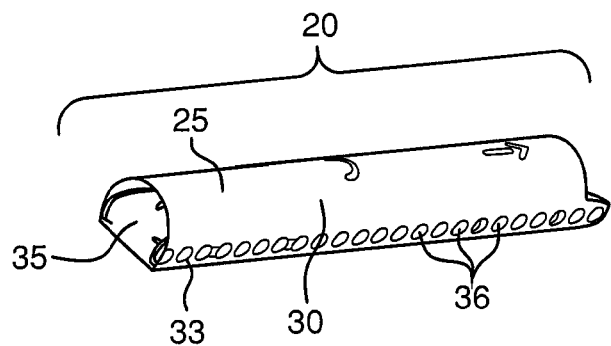
FIG. 3 is a three-quarter isometric view of another embodiment of a surgical staple line reinforcement of the present invention.

As shown in FIG. 3, the circles are ultrasonic weld dots and part of the stiffening member. The perforations are at about the 90 degree bend in the material below the dots. An ultrasonic welding device may be used to form the dots. The staple line reinforcement of claim 1 may comprise a means to allow separation of the face 30 of the tubular structure 25 away from a remainder of the tubular structure after insertion. In the embodiment, depicted in FIG. 3, this means comprises parallel lines of perforations 36 which permit separation of the face 30 from the tubular structure. The perforations are preferably staggered relative to each other to resist longitudinal compression of the tubular structure.

Figure 4:
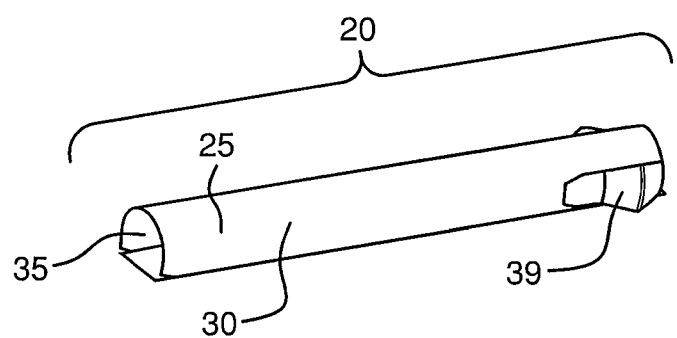
FIG. 4 is a three-quarter isometric view of still another embodiment of a surgical staple line reinforcement of the present invention.

As shown in FIG. 2 and FIGS. 4 and 5, the staple line reinforcement of the present invention may further comprise a tab or loop 39, respectively, to assist in separation of the face 30 from the remainder of the tubular structure 25 after insertion.

Preferably, the tubular structure is constructed from porous polytetrafluoroethylene (PTFE), and particularly a stretched or expanded PTFE such as that made in accordance with U.S. Pat. Nos. 3,953,566, 3,962,153, 4,096,227, and 4,187,390, all incorporated by reference. By heating and rapidly expanding PTFE in accordance with the teachings of these patents, the resulting material exhibits exceptional strength in the direction that it has been expanded. A preferred tubular structure is formed from a porous PTFE, and most preferably an expanded PTFE. However, as will be understood by the skilled artisan upon reading this disclosure, other bio-implantable materials can be used. Examples of other possible implantable materials that may be employed with the present invention include, but are not limited to, nylon; polypropylene; polyurethane; silicone; DACRON® polymer; etc. For some applications, it may be desirable to use a bio-absorbable implantable material, such as polyglycolic acid (PGA), polylactic acid (PLA), polycaprolactone, or natural animal membranes.

Most desirable in production of the staple line reinforcement of the present invention is use of a very thin implantable material for the tubular structure, and in particular the face, to leave the least amount of foreign material in the body.

However, thin materials lack adequate column strength of their own to resist movement, rotation, or longitudinal compression (bunching) during manipulation, positioning, and deployment of the staple line reinforcement.

Accordingly, in the present invention, one or more stiffening members are attached to or integrated with the tubular structure. The stiffening member preferably extends from one end of the tubular structure to the other end and is located at the bottom of the tubular structure. In embodiments comprising a separating means, the stiffening member may be adjacent and extend parallel with respect to such means. The stiffening member comprises a stiffer implantable material as compared to the tubular structure which resists movement, rotation, or longitudinal compression of the tubular structure. The stiffening member may comprise the same material as the tubular structure at a different thickness. Alternatively, the face and stiffening member may comprise different materials.

It is particularly preferred that the staple line reinforcement of the present invention includes means to allow separation of the attached face of the tubular structure from the remainder of the staple line reinforcement following actuation of the stapler. This can be accomplished in a number of ways. The tubular structure of the staple line reinforcement may be modified during its formation to selectively weaken certain areas so that they will readily rip longitudinally. Where the tubular structure is being created by extrusion, this can be accomplished by modifying the extrusion die to reduce the thickness of the tubular structure in certain areas to create tear lines. For instance, one or more projections may be provided into the flow of extrudate passing through the die that will reduce the thickness along longitudinal lengths of the tubular structure being produced. These longitudinal lengths will thereby be weakened, allowing the material to more readily separate (or "tear") along these lengths. Any structure that will provide for controlled separation of material in this manner is referred to herein as a "tear line."

Another method of creating tear lines is to produce the tear lines following creation of the tubular structure. This can be accomplished by stripping or modifying the tubular structure material in the places where tears are desired, such as through: selective heating or altering of the tubular structure material to create the tear line (e.g., through use of a laser or heated cutting implement); cutting the tubular structure to a prescribed depth along the desired tear line (e.g., with a cutting blade); mechanically altering the material (e.g., through use of pinch rollers); selectively weakening the material; etc.

Alternatively, the tubular structure may be scored with lines of holes or similar structures that will provide sufficient weakening to allow easier separation of remainder portions of the sleeve following installation. This can be accomplished through a number of means, such as: creating holes with lasers; punching holes; using a pinch roller with teeth; etc.; or through some combination of any of the methods described.

Once tear lines are created, separation of material following insertion can be easily and rapidly accomplished.

The exact shape and dimensions of the staple line reinforcement of the present invention are a function of the particular constraints of the surgical apparatus and procedures with which it is to be employed. As such, the reinforcement device of the present invention may be formed in virtually any shape or size, including cross-sections comprising a circle, semi-circle, oval or other oblong shape, triangle, rectangle, pentagon, hexagon, etc., or some less defined shape. Further, the face or faces and tubular structure of the staple line reinforcement need not be entirely planar, and may include folds or other essentially concave or convex orientations. In fact, folds or concave wall structure may be useful in some embodiments in order to assure more secure grip of the stapler arms by the staple line reinforcement.

While the staple line reinforcement of the present invention may be provided in a plethora of different shapes and sizes to fit different types of surgical stapler arms, it is believed that the staple line reinforcement depicted in FIGS. 2 through 5 particularly lends itself to use with means to hold the staple line reinforcement on a variety of different stapler arm sizes and shapes.

The present invention can be used in a host of surgical procedures. Among the possible usages are: various lung resection procedures (e.g., blebectomies, lobectomoies, bullectomies, wedge resections, and lung reduction procedures, such as those used to treat symptoms of emphysema); treatment of soft tissue injuries and defects (e.g., abdominal or thoracic wall procedures, gastro-intestinal procedures); and as a tool in a variety of other surgical procedures (e.g., reproductive organ repair procedures, etc.). The staple line reinforcements may be used with either anastomotic staplers or non-anastomotic staplers. Naturally, the staple line reinforcement of the present invention may be used in conjunction with operations on both humans and animals.

It should be appreciated that while the staple line reinforcement of the present invention may be used in pairs, as shown in FIG. 1, it is believed that it may also be beneficial to use it to reinforce only one side of certain procedures. For example, the staple line reinforcement may be installed on only one side of a surgical seam joining tissue or devices where a weak material is being attached to a relatively strong material (i.e., certain relatively weak tissue or prosthetic devices that may be prone to tear along staple lines may be attached to relatively strong tissue or devices that are not so inclined to tear). In these instances, a staple line reinforcement of the present invention can be provided to cover only the material prone to staple damage. Without compromising seam integrity, this allows for a thinner overall seam and reduces the amount of material placed in the patient.

It should be noted that various other materials may be added to the staple line reinforcement of the present invention to provide additional utility. For example, an antimicrobial or antibiotic agent may be coated on and/or filled within the porous structure of the tubular structure to provide assistance in avoiding infection. This is considered to be particularly useful in various procedures (e.g., intestine resections, surgery on trauma injuries (e.g., chest or abdominal trauma), etc.) where microbial or bacterial infection is likely. Other useful additives may include adhesives, radio-visible compounds, clotting agents, agents promoting healing, cancer treating agents, etc.

While particular embodiments of the present invention have been illustrated and described herein, the present invention should not be limited to such illustrations and descriptions. It should be apparent that changes and modifications may be incorporated and embodied as part of the present invention within the scope of the following claims.

What is claimed is:

1. A staple line reinforcement comprising a tubular structure having at least one operative face proportioned to reinforce surgical staples at a surgical site and one or more stiffening members attached to or integrated with the tubular structure to resist, prevent, or inhibit movement, rotation, or longitudinal compression of the tubular structure comprising a means to allow separation of the face of the tubular structure away from a remainder of the tubular structure after insertion wherein said means comprise parallel lines of perforations to allow separation of the face from the tubular structure wherein the perforations are staggered relative to each other to resist longitudinal compression of the tubular structure.

2. The staple line reinforcement of claim 1 wherein the face comprises a thin compressible material and the stiffening member comprises a stiffer material which resists movement, rotation, or longitudinal compression of the tubular structure.

3. The staple line reinforcement of claim 2 wherein the face and stiffening member comprise different materials.

4. The staple line reinforcement of claim 1 further comprising a loop or tab to assist in separation of the face from the remainder of the tubular structure after insertion.

* * * * *

UNITED STATES PATENT AND TRADEMARK OFFICE
CERTIFICATE OF CORRECTION

PATENT NO. : 8,317,790 B2
APPLICATION NO. : 12/208394
DATED : November 27, 2012
INVENTOR(S) : Bell et al.

It is certified that error appears in the above-identified patent and that said Letters Patent is hereby corrected as shown below:

In the Specification

Column 1, lines 29 & 30: delete "4,652,245" should read --4,452,245--

Signed and Sealed this
First Day of October, 2013

Teresa Stanek Rea
*Deputy Director of the United States Patent and Trademark Office*